(12) United States Patent
Orten

(10) Patent No.: US 8,105,248 B2
(45) Date of Patent: Jan. 31, 2012

(54) MEDICAL PLASTER

(75) Inventor: Birger Orten, Alesund (NO)

(73) Assignee: Orga Sense AS, Drammen (NO)

( * ) Notice: Subject to any disclaimer, the term of this patent is extended or adjusted under 35 U.S.C. 154(b) by 1415 days.

(21) Appl. No.: 10/398,849

(22) PCT Filed: Oct. 15, 2001

(86) PCT No.: PCT/NO01/00416
§ 371 (c)(1),
(2), (4) Date: Jun. 25, 2003

(87) PCT Pub. No.: WO02/38216
PCT Pub. Date: May 16, 2002

(65) Prior Publication Data
US 2004/0030267 A1    Feb. 12, 2004

(30) Foreign Application Priority Data
Oct. 16, 2000 (NO) .................................. 20005205

(51) Int. Cl.
*A61H 1/00* (2006.01)
(52) U.S. Cl. .................. 601/2; 601/3; 601/4; 607/2
(58) Field of Classification Search ............ 601/2, 3, 601/4; 607/2, 46, 48, 50; 128/907; 600/554
See application file for complete search history.

(56) References Cited

U.S. PATENT DOCUMENTS

| 4,317,457 | A   |   | 3/1982  | Guillot        |         |
|-----------|-----|---|---------|----------------|---------|
| 4,787,847 | A   | * | 11/1988 | Martin et al.  | 433/119 |
| 4,823,810 | A   | * | 4/1989  | Dervieux       | 607/46  |
| 5,048,527 | A   |   | 9/1991  | Okazaki        |         |
| 5,365,937 | A   |   | 11/1994 | Reeves et al.  |         |
| 5,578,065 | A   | * | 11/1996 | Hattori et al. | 607/46  |
| 5,656,016 | A   | * | 8/1997  | Ogden          | 601/2   |
| 5,904,659 | A   |   | 5/1999  | Duarte et al.  |         |
| 5,957,854 | A   | * | 9/1999  | Besson et al.  | 600/509 |
| 6,289,238 | B1  | * | 9/2001  | Besson et al.  | 600/509 |
| 6,575,956 | B1  | * | 6/2003  | Brisken et al. | 604/500 |
| 6,719,694 | B2  | * | 4/2004  | Weng et al.    | 600/439 |
| 6,847,836 | B1  | * | 1/2005  | Sujdak         | 600/382 |
| 6,937,893 | B2  | * | 8/2005  | Danz et al.    | 607/3   |
| 2002/0082668 | A1 | * | 6/2002 | Ingman         | 607/98  |
| 2004/0015058 | A1 | * | 1/2004 | Besson et al.  | 600/301 |
| 2004/0039343 | A1 | * | 2/2004 | Eppstein et al.| 604/200 |

FOREIGN PATENT DOCUMENTS

| DE | 3221145   | 12/1982 |
| EP | 0367320   | 5/1990  |
| EP | 0699453   | 6/1996  |
| EP | 1060728   | 12/2000 |
| WO | WO9962402 | 12/1999 |
| WO | WO0044437 | 8/2000  |

* cited by examiner

*Primary Examiner* — Brian Casler
*Assistant Examiner* — Nasir Shahrestani
(74) *Attorney, Agent, or Firm* — Ladas & Parry LLP (57) ABSTRACT

A piezoelectric unit (4), preferably a piezoelectric foil, is arranged in a medical plaster unit (13) for therapeutic or stimulating influence of body tissue in an area underneath the plaster unit. The plaster unit may be equipped with a battery (11) and a microcircuit (2) for delivering voltage pulses or oscillations to the piezo unit (4). The plaster unit (13) can possibly be used as part of a system of several plaster units (13) that are activated synchronously to influence one and the same tissues area.

19 Claims, 9 Drawing Sheets

MEDICAL PLASTER

The present invention relates to influence, preferably therapeutic influence, on tissue in a living being, from the outside of the skin, and more particularly the invention is directed to a medical plaster or a medical plaster system that is capable of delivering mechanical vibration energy and/or electrical energy to body tissue from the outside of the skin.

The body tissue may comprise skin tissue (wound areas), muscle tissue, glands, bone tissue and internal organs, including the brain. "Body" is intended to mean bodies of living animals and humans, possibly also plants.

Regarding use of the plaster/plaster system in accordance with the invention, one may visualize for instance treatment of incontinence, influencing the pancreas, muscle stimulating and assuaging uses, foot zone therapy, skin wound treatment etc.

Adhesive pads for picking up electrical signals from living tissue and organs are previously known, compare ordinary ECG equipment, but firstly this concerns receiving energy, not transmitting energy, and secondly, receiving electrical signals only.

From U.S. Pat. No. 4,317,457 is previously known a system for electrical and therapeutic treatment of body tissue, i.e. conducting an electrical current through a body area by means of two electrodes held in position by means of a single-use cast that is adapted to the body area.

From U.S. Pat. No. 4,823,810 is known a therapeutic system with discharge of sparks against the skin, as a form of acupuncture. Even if it is stated that the sparks are generated by means of a piezoelectric generator, this system deals in reality with electric energy applied to the body tissue by means of needle electrodes or electrodes in the form of sawtooth-edged blades.

Finally, from U.S. Pat. No. 5,048,527 is known an apparatus for therapeutic crushing of for example kidney stones by means of shock waves (ultrasound) generated for instance by a piezoelectric transducer. However, the apparatus is large, and comprises inter alia a water tank in a bellows, the water in the bellows constituting a coupling medium between the transducer and the skin surface of the patient.

There exists a need of an equipment for therapeutic influence by means of mechanical vibrations that is more patient-friendly, than the equipment types present until now. The present invention has been provided for this purpose, and the invention comprises a medical plaster such as defined in the appended claim 1, and a medical plaster system such as defined in appended claim 7. Favorable embodiments of the two aspects of the invention appear from the dependent claims, and from the description following hereafter.

In the following, the invention shall be described in closer detail by discussing embodiment examples while referring to the appended drawings, of which

Figure 1:
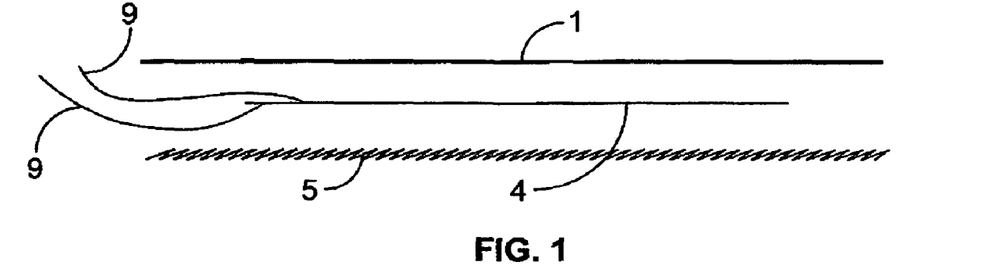
FIG. 1 shows, as a cross-sectional sketch, a basic embodiment of a medical plaster in accordance with the invention, various layers of the plaster being shown in an exploded view, and including a piezoelectric unit.

Referring to FIG. 1, a simple and basic embodiment of the invention is described, taking as a starting point an ordinary and well known medical plaster (adhesive plaster) consisting of a backing layer 1 of a fabric or a plastic material, and a front layer 5 that is an adhesive substance of a previously known type. In accordance with a simple embodiment of the invention, a piezoelectric foil 4 has been added in between the two layers mentioned above. In order to work, this foil must have a supply of electric voltage, i.e. in order to produce mechanical vibration, a time-varying voltage must be applied to the two sides of the foil, and supply wires 9 are shown, protruding from the end of the plaster. An outer, not shown energizing circuit can be connected to these wires 9 to activate the foil 4. The termination to the very foil 4 is only shown in a schematic manner, and special conductor patterns/metallizations on both sides of foil 4 are used in order to obtain various vibration modes, but these details are not explained further here. Such metallization and wiring can be made very thin and foil-like, so that the device does not need to extend very much in thickness/height, but may look like an ordinary plaster.

However, it is to be noted at the same time that these considerations shall not constitute any restriction regarding the invention, this invention also comprising plasters in which certain parts that will be mentioned subsequently, extend somewhat outwards/upwards, in such a manner that for instance central parts or edge parts of the plaster will be "thick".

In this connection it should also be mentioned that the piezoelectric foil 4 can be replaced by other piezoelectric units, for instance bimorph elements, which may result in thicker plaster embodiments. However, in the preferred embodiments illustrated here, polymer foil is used.

Figure 2:
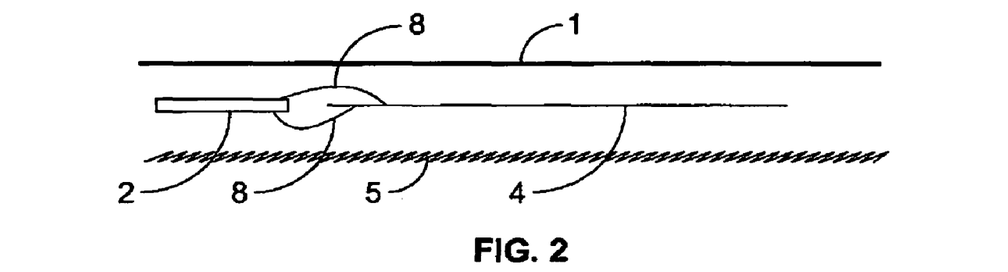
FIG. 2 shows, in the same form as in FIG. 1, an embodiment of the plaster in accordance with the invention, with its own energizing circuit included.

The embodiment in FIG. 1 depends on an external energizing circuit, but in FIG. 2 appears an embodiment of a self-sufficient type. This influence-plaster has, as a substitution for the outgoing wires 9 in FIG. 1, its own energizing circuit 2, which circuit also comprises an energy source (a battery). Hence, supply conductors 8 exist only between circuit 2 and foil 4. Preferably, energizing control is executed in accordance with internal pre-programming in a microcircuit included in the energizing circuit. Suitably, the process is started when the plaster is applied to the skin area in question, either by finger-operated activating of a (not shown) microswitch, or suitably automatically by removing a cover layer from the adhesive substance 5 (see cover layer 7 in FIG. 7). The cover layer may for example in a simple manner, have en insulating edge folded in between two resilient conductors near the battery, in such a manner that the battery is switched in, thereby starting the process, when the cover layer is picked away.

Figure 8:
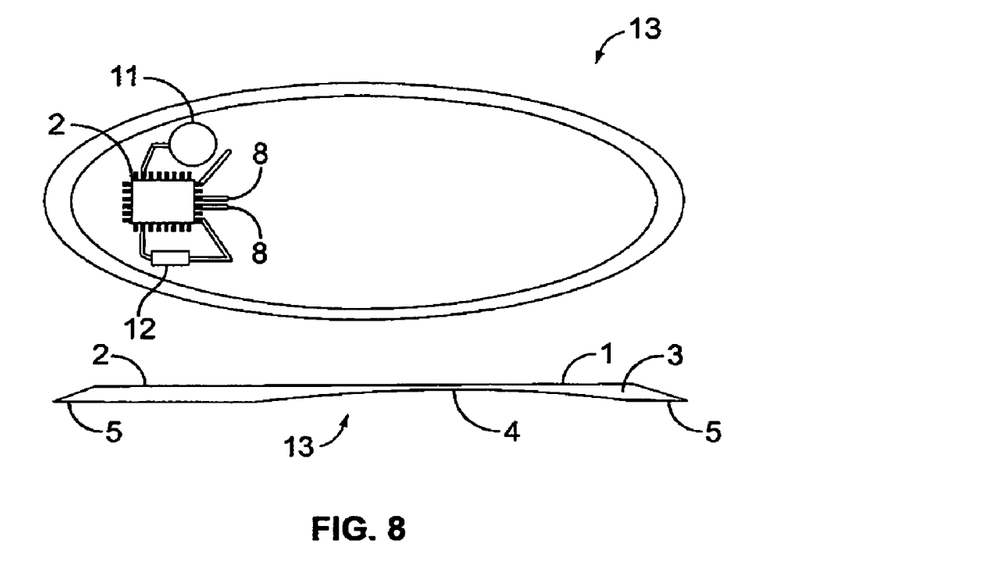
FIG. 8 shows a more practical embodiment of a plaster in accordance with the invention, substantially in accordance with a combination of FIG. 2 and FIG. 5, in a view from above/outside and in a sectional side view.

The energizing circuit 2, shown as a substantially flat unit, however with a certain thickness relative to for instance the preferred piezo-foil 4, is only shown in a schematical manner, and is intended to comprise for instance such elements as shown in FIG. 8, viz. a microprocessor, a battery and possibly a special capacitor for charging to a high voltage. With today's technology it is also possible to manufacture microprocessor circuitry and capacitors almost in a foil configuration, so that the thickness can be made quite small also for these elements. (Additionally, using a foil-shaped energizing circuit 2, one may obtain the advantage that the need of conductors 8 is removed, i.e. foils 2 and 4 can then virtually be integrated to one connected sheet.) A battery will, with today's technology, often exhibit some thickness, but the present invention does not impose any limitations at this point.

Figure 3:
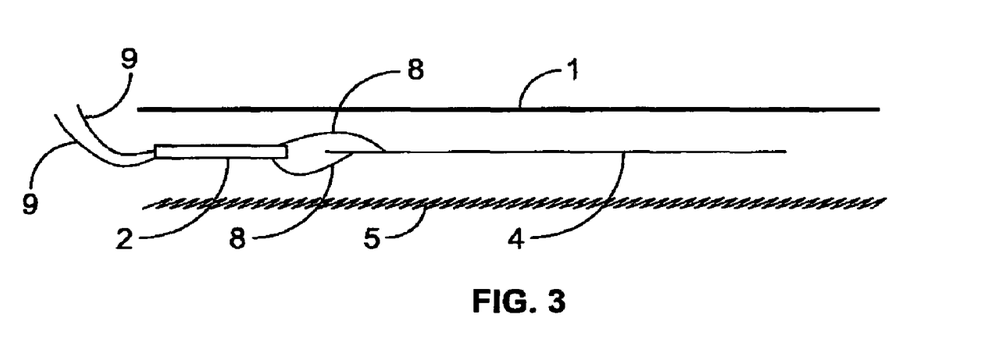
FIG. 3 shows, in a similar manner, an embodiment in which an inlaid energizing circuit has outgoing cable connections.

FIG. 3 shows a variant having a built-in energizing circuit 2, but with outgoing wires 9, for the following possible purposes: a) supplying power from another plaster having a battery, or from an external power supply unit, b) transferring power from the plaster's own battery to another plaster, c) transmitting a control or synchronizing signal from an energizing circuit in another plaster ("superior" energizing circuit), or from an external operation control unit (that may be the same unit as the power supply unit mentioned above), d) transmitting a control or synchronization signal to another plaster (which is then a "subordinate" plaster). It is of course possible to combine the features mentioned here, i.e. simultaneous supply of operating power for the energizing circuit, i.e. for running a microprocessor and for charging a capacitor, and transmitting control signals for synchronized trigging of piezo-pulses.

Figure 4:
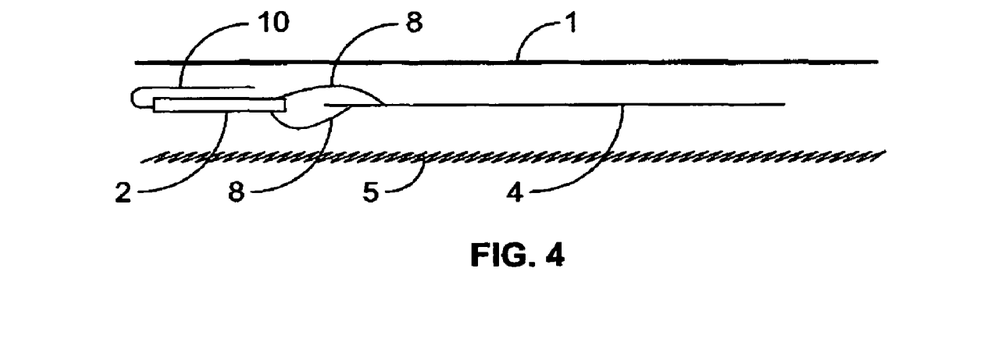
FIG. 4 shows in a similar manner an embodiment in which an inlaid energizing circuit has an antenna for exchange of control signals.

In FIG. 4 appears an embodiment in which the energizing circuit 2 is self-supplied with regard to energy, i.e. it is provided with a battery, but an antenna 10 takes care of wireless reception of control signals from the outside, or it is a sending antenna for transmission of a control signal for synchronizing other plasters nearby having reception antennas. The remaining elements in the plaster are repeated from previous drawings.

Figure 5:
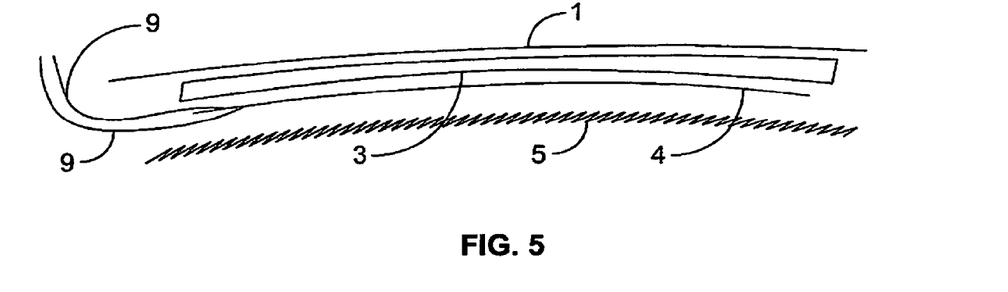
FIG. 5 shows in a similar manner an embodiment with a rear mass laid in behind a piezoelectric unit.

FIG. 5 shows a medical plaster of the same kind as in FIG. 1, however a backing mass 3 has been laid in, which backing mass has as its main function to provide for radiating a larger part of the emitted energy from the piezo-element "downwards", i.e. into the skin and not out in the opposite direction. Therefore, the backing mass 3 must have a higher density than foil 4, and it should be at least ten times as thick as the foil. A standard thickness for a piezoelectric foil is 28 µm, and with such a foil 4, the backing mass should consequently have a thickness of at least about 0.3 mm.

Besides, in FIG. 5 the backing mass 3 is drawn with a thickness that is gradually diminishing towards the center from both edges (i.e. $\geqq 0.3$ mm in the central part), this because a parabolic shape, to be engaged by the piezoelectric foil 4 itself, will cause some focusing of irradiated energy into the tissue thereunder. Of course, such a variant of the plaster in accordance with the invention will result in a plaster that is somewhat stiffer, but no restriction should be made here regarding lateral dimensions. Hence, such backing masses may be sectioned and also in such a manner that the foil yields along with several focusing backing mass areas. But even with only one such parabolic backing mass area, the plaster is able to work in accordance with its purpose, for example with a (not shown) filling area in front of (below) the foil 4, so that the adhesive substance 5 nevertheless is mounted in a substantially flat manner, and is able to adhere to a substantially flat skin area. (Furthermore, a substantially parabolically shaped plaster may fit very well in some body areas.)

Figure 6:
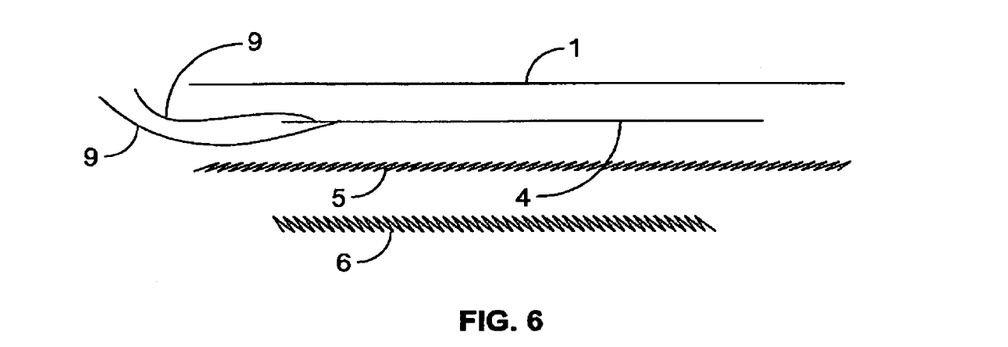
FIG. 6 shows in a similar manner an embodiment with a contact gel as an additional front layer.

FIG. 6 shows another optional feature, namely a contact gel 6, preferably to be applied just before applying the plaster, and that to a certain degree also may provide filling under an arcuate parabolic shape as mentioned above.

Figure 7:
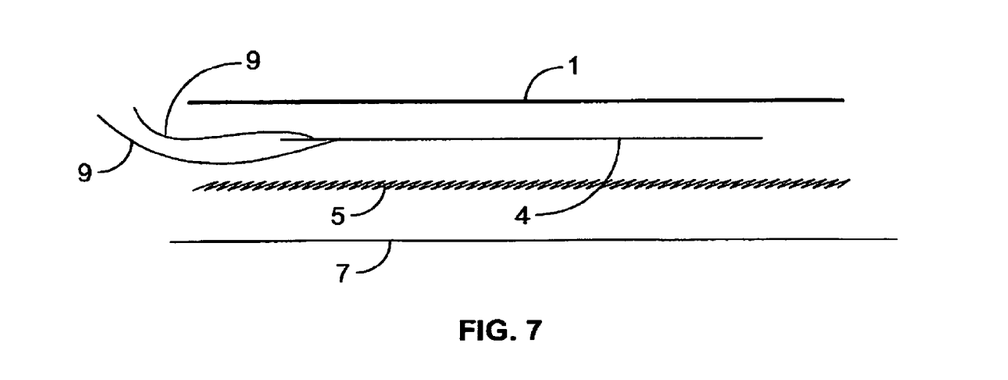
FIG. 7 shows in a similar manner the basic embodiment of FIG. 1 with a removable protective sheet as a front layer.

In FIG. 7 appears an element that is often necessary for a plaster unit having an adhesive side, namely a protective cover layer 7 to be peeled off when the plaster shall be put into use, i.e. in order to expose the adhesive surface.

Several of the features shown in FIGS. 1-7 can be combined as appropriate. For instance, in most embodiments the plaster will be supplied with a cover tape 7 as shown in FIG. 7, and when this cover tape has been removed, in many cases it will be of interest to apply a contact gel 6 as shown in FIG. 6. In preferred embodiments, the plaster will have a backing mass 3 in accordance with FIG. 5, and this backing mass will possibly have a parabolic shape. In addition, an energizing circuit will often be included, such as in FIGS. 2, 3 or 4.

In FIG. 8 appears an embodiment to be considered as corresponding to FIG. 2 plus FIG. 5 (possibly FIG. 4 plus FIG. 5), designed as a plaster 13 having an oval shape and with a parabolic underside, with an energizing circuit on the other side, with a separate micro processor 2, battery 11 and charging capacitor 12. However, in the embodiment shown here, the plaster has an adhesive layer 5 only in a "band" along the plaster periphery. When the plaster 13 is adherently and strongly attached along the periphery, a skin area underneath the parabolic part will usually be pushed somewhat up to fill out "the cavity", and additionally it will be a natural thing to use a contact gel underneath the parabolic area.

Figure 9:
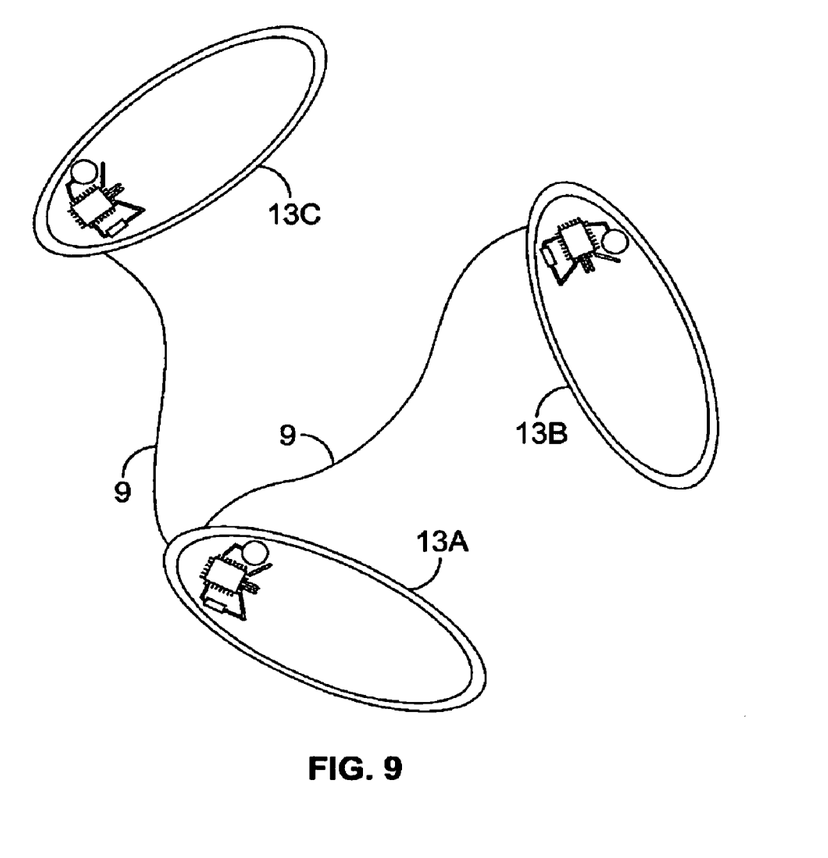
FIG. 9 shows three such plasters as shown in FIG. 8, in the form of a mutually cable-connected plaster system in accordance with an embodiment of the invention.

In FIG. 9 appears a group of three such plaster units 13a, 13b and 13c, of which unit 13a is a superior unit providing control, i.e. synchronized operation for the three units. The goal is to influence for instance a deeply situated tissue area simultaneously from all three units (or in controlled succession). In this embodiment, every plaster unit has its own microcircuit and battery, so only control signals are necessary from 13a to 13b and 13c. However, in a related variant, 13b and 13c are also without battery, so that the battery in 13a will also power the circuits of 13b and 13c. In a further variant, 13b and 13c are of a quite simple type, such as shown in principle in FIG. 1 (however possibly with a parabolic geometry/backing mass like in FIG. 5), and then 13b and 13c are operated completely from 13a.

Figure 10:
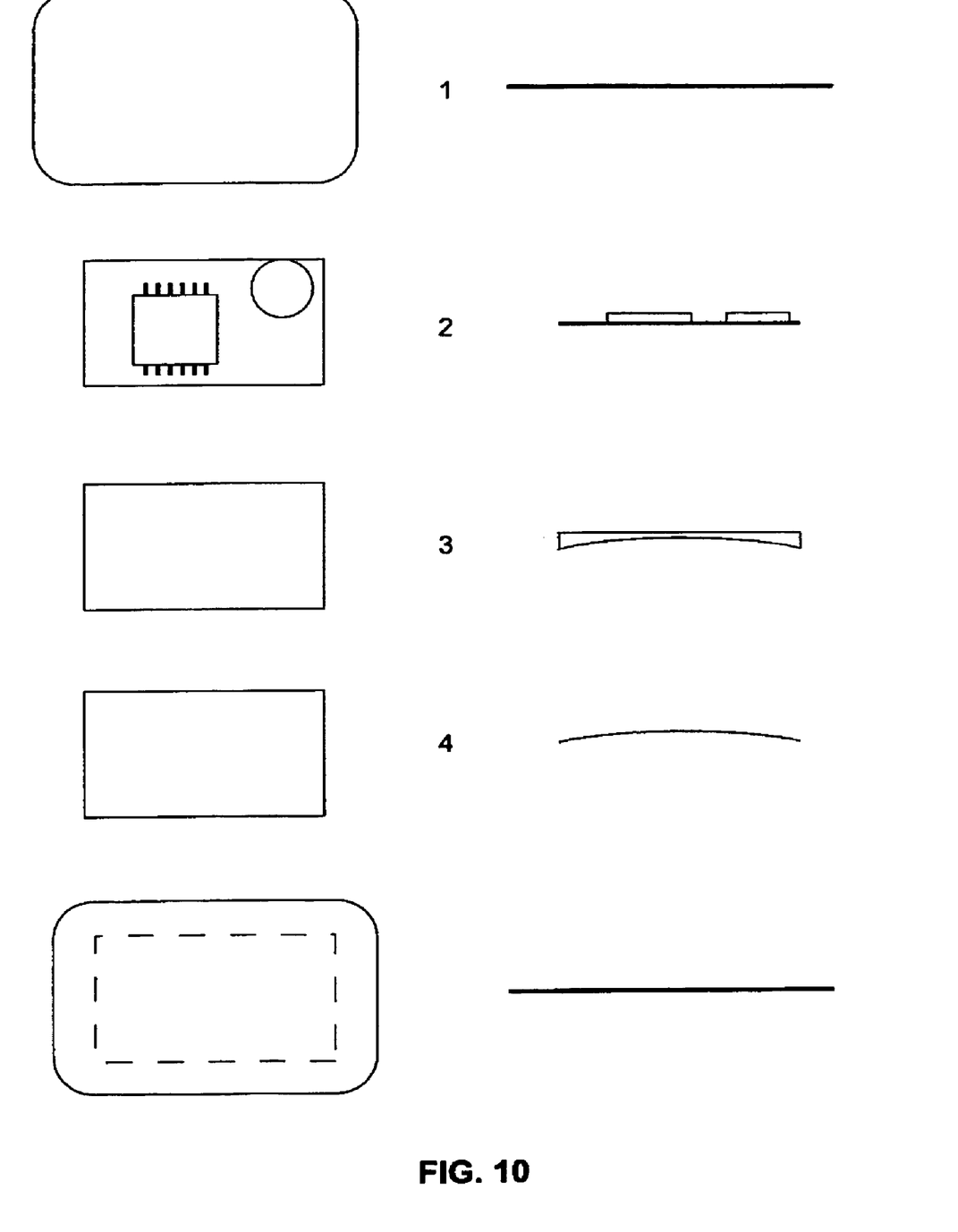
FIG. 10 shows, layer over layer and both in a top view and a side view, a further embodiment of a medical plaster in accordance with the invention.

FIG. 10 shows the construction of another embodiment of a medical plaster in accordance with the invention, layer by layer: On top a cover layer 1 as previously mentioned, thereafter a layer in which the energizing circuit 2 is situated. In this case, the energizing circuit 2 is distributed laterally as a separate layer, that may be quite flat as previously mentioned, or it may build to a certain height.

Thereafter, the backing mass layer 3 follows, also in this case shown having a parabolic shape, and the piezo-polymer foil 4 thereunder takes on the same shape. Thereafter comes the adhesive layer 5, and a contact gel area such as in FIG. 6, reference numeral 6, is indicated by a broken line square in the center thereof.

Figure 11:
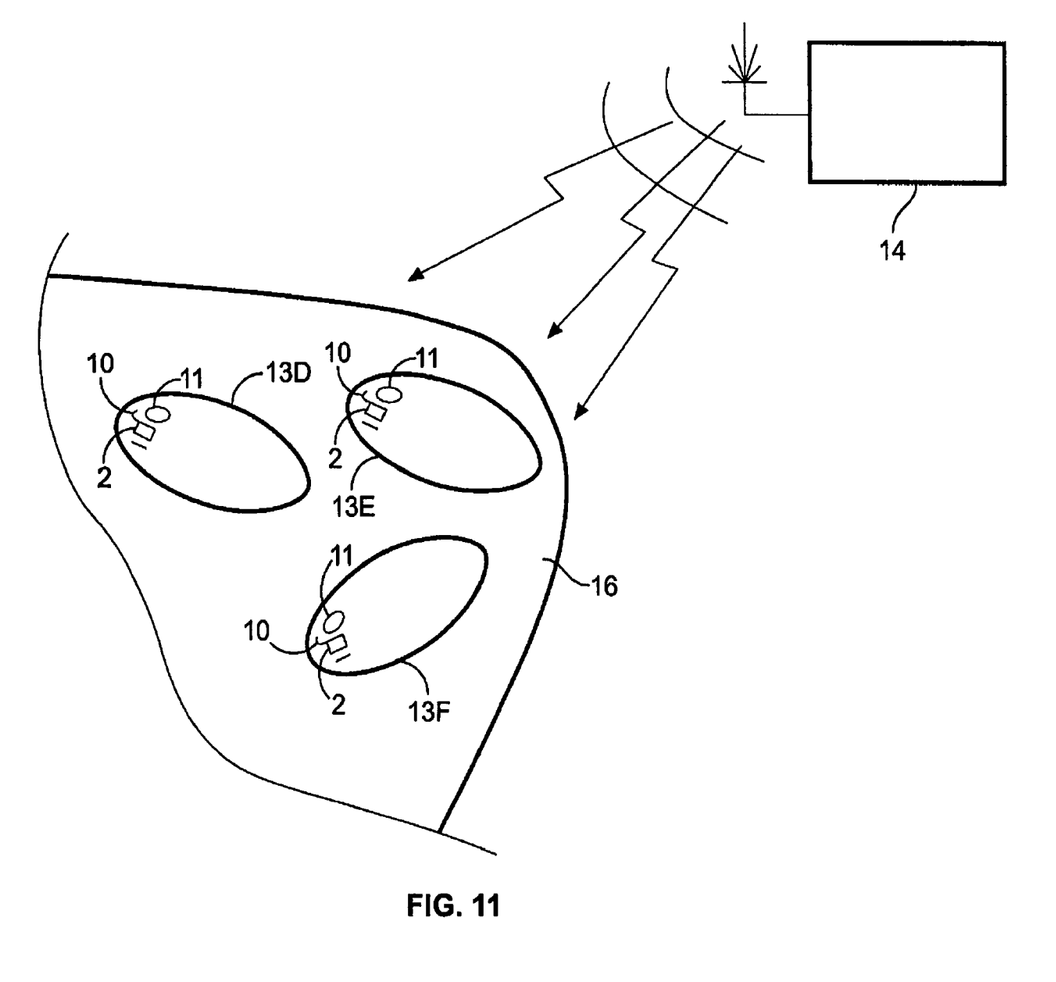
FIGS. 11, 12 and 13 show examples of plaster systems in accordance with the invention.

In FIG. 11 appears, as a sketch, an embodiment of a plaster system in accordance with the invention, in which three plaster units 13d, 13e and 13f, provided on a body part 16, all have their own energy supply (battery), but control is executed in a wireless manner from an external control unit 14, reception antennas 10 being attached to every microcircuit 2.

Figure 12:
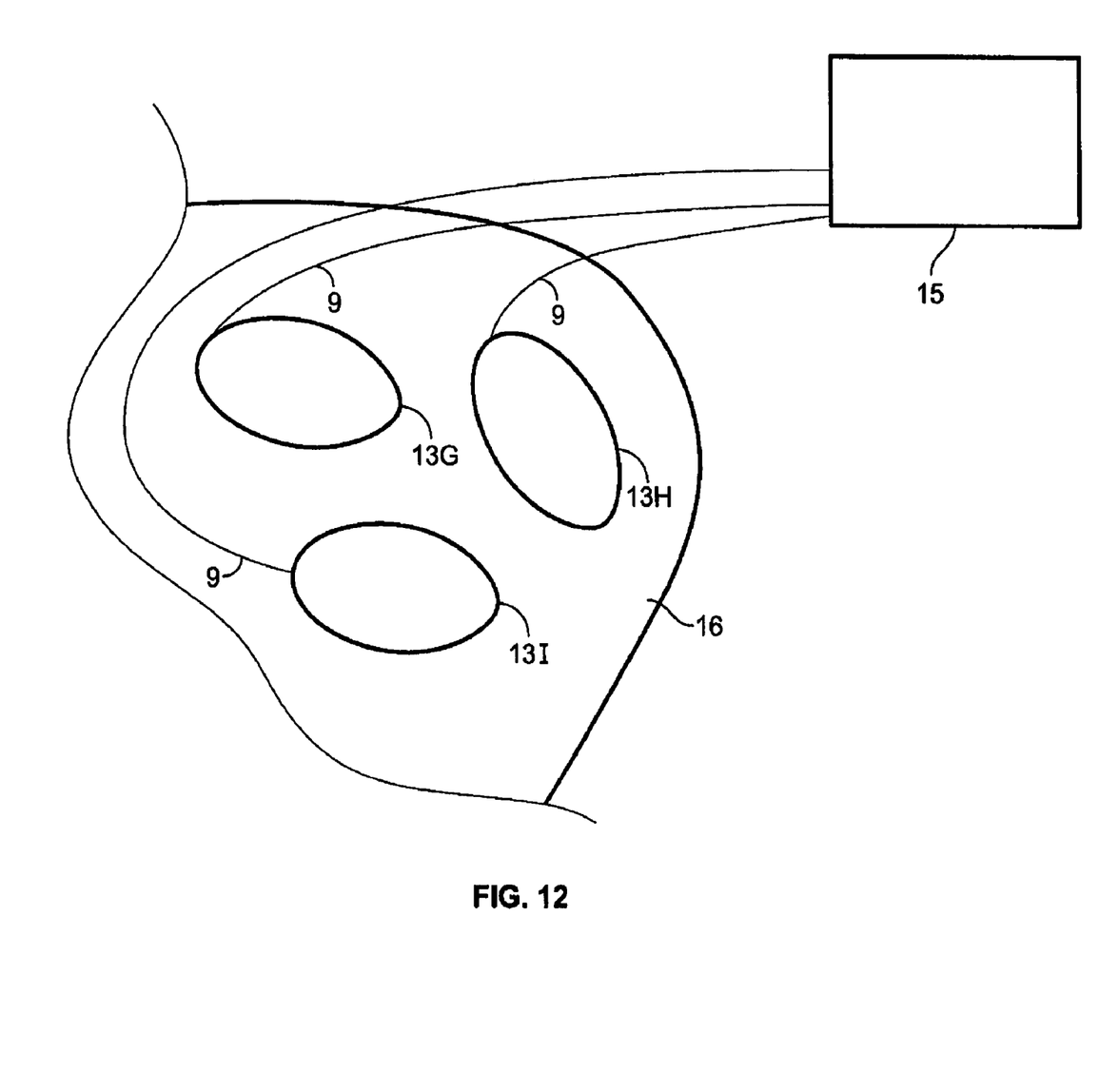

FIG. 12 shows in a similar manner an embodiment of a plaster system in accordance with the invention, in which three simple plaster units 13g, 13h and 13i, arranged on a body part 16, are operated completely by means of an external operating unit 15.

Figure 13:
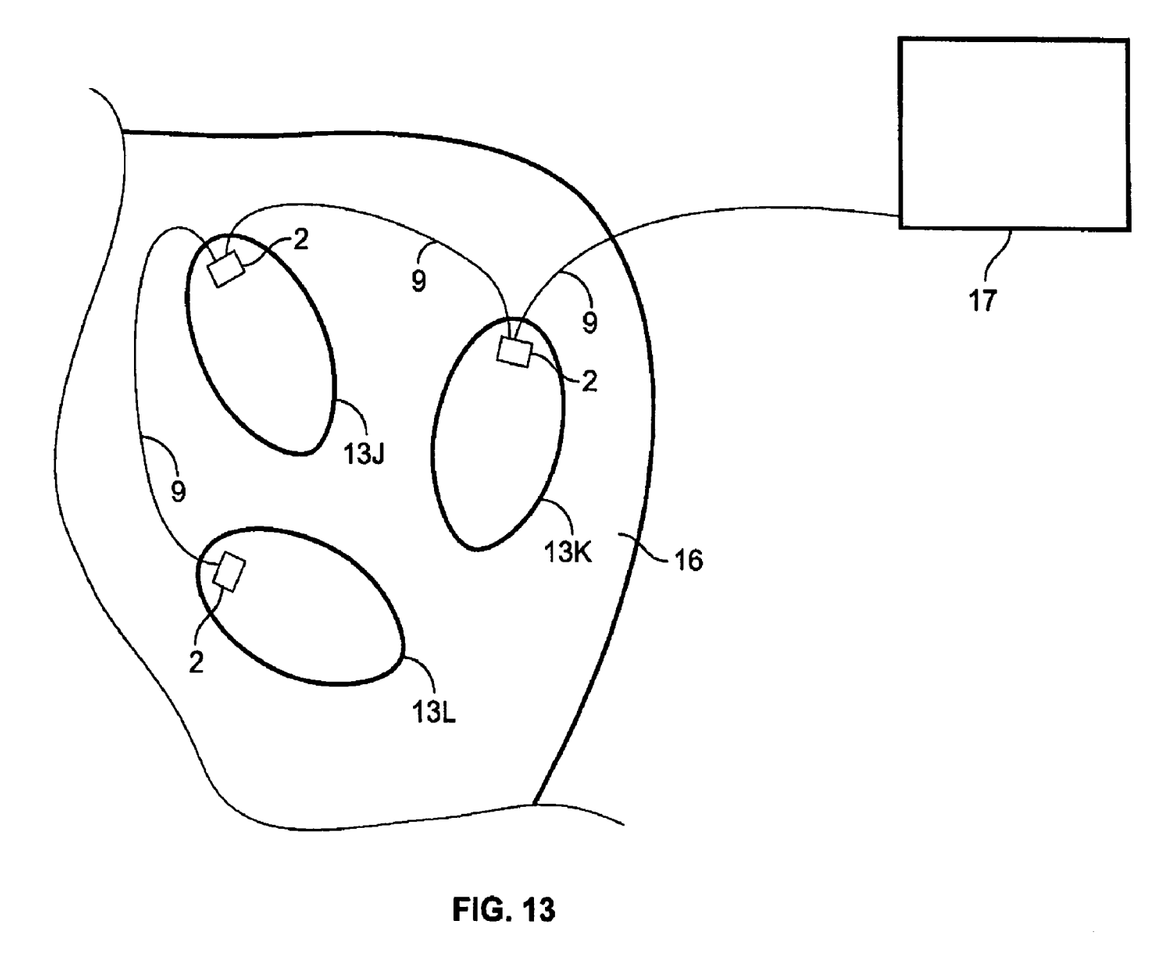

FIG. 13 shows another embodiment, wherein plaster unit 13j, 13k and 13l are without batteries, receiving power from an external operating unit 17 like in the previous case, but wherein every plaster unit has its own energizing circuit 2. In this case, the energizing circuit in for instance plaster unit 13k may be a superior energizing circuit, taking care of synchronization, or synchronization may possibly come from operating unit 17.

It seems unnecessary to explain every possible combination for such a system by means of drawings, and all combination possibilities should be regarded as described through the above detailed description of possible single features.

Figure 14:
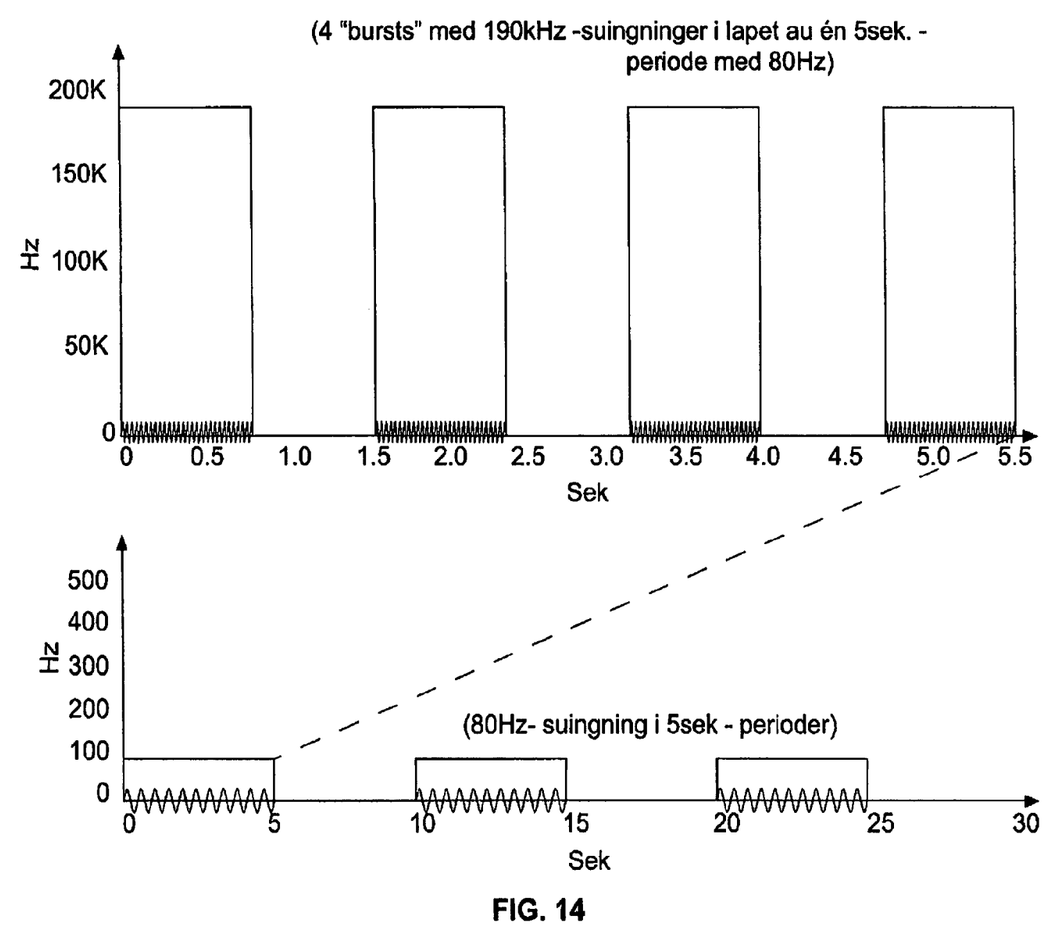
FIG. 14 shows an example of a drive frequency pattern applied to the piezoelectric unit in a plaster in accordance with the invention.
Figure 15:
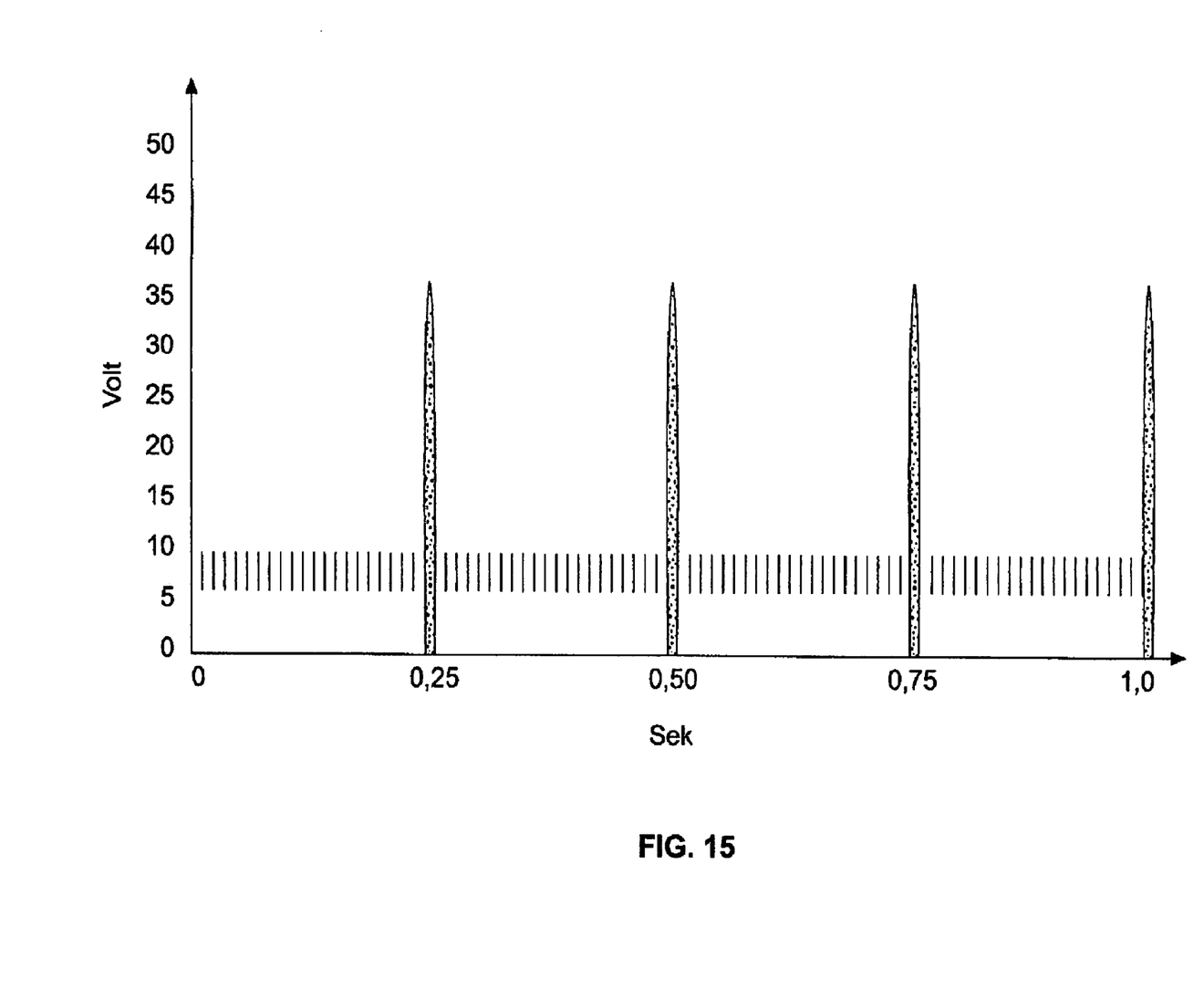
FIG. 15 shows an example of voltage variations in the case illustrated in FIG. 14.

Energizing of the piezoelectric unit 4 usually takes place in the form of bursts of ultrasonic oscillations in the range 100 kHz-3 MHz, superposed on a slower oscillation, for example an 80 Hz sine wave. FIGS. 14 and 15 show, in illustrative manner only, typical frequency and voltage curves, with a horizontal time axis and frequency and voltage respectively, along the vertical axis. The values that appear, shall only be considered as examples, and are not intended to be limitative. In FIG. 14 appears, in the lower part of the drawing, a basic oscillation of 80 Hz, running in periods of 5 seconds and with intervals of 5 seconds. Superposed on this basic oscillation appears, in the top part of the drawing, 4 bursts being applied during a 5 second period, and every such burst consists of a very rapid oscillation (190 kHz), illustrated sketch-like by rapid oscillations on the time axis. Please note that the oscillations illustrated are purely illustrative and not drawn to scale. Besides, the vertical axis is in hertz, whereas the oscillations are actually voltage oscillations. However, in FIG. 15 appears a voltage diagram showing that the 80 Hz oscillation takes place between 6 and 9 volt, whereas the high frequency bursts are applied with a maximum voltage, approximately 37 volt.

It must be emphasized once more that numerical values of the parameters of interest, i.e. voltages, frequencies and time, are only intended as illustrative and exemplary values here, and they shall not restrict the invention in any manner. Limitations regarding the invention will appear only in the appended patent claims.

Plaster units in accordance with the invention will give a patient the possibility for instance to execute self-therapy when the plasters have been mounted and their function checked. For example, in the simplest embodiment without a battery, i.e. with an external operating unit, such a possibility exists. The operating unit may possibly be portable and operable by means of a switch, or wires going out from the plaster units may be connected to the operating unit in a simple manner, and the operating unit thereafter activated. Hence, there should be no problem regarding executing self therapy during a time span of 1-2 weeks, for instance 3-4 times per week, without having to go to a number of appointments with a therapist, when the therapist has first mounted the plaster units and checked their function.

In certain cases it may be favorable with an additional elastic bandage outside the plaster unit of the invention, or outside the plaster system of the invention, in order to provide extra support and increased effect by tightening the bandage.

In the introduction, interesting therapy areas were mentioned, like treatment of incontinence, pancreas problems, skin wounds and muscle pains, in addition to foot zone therapy. It is also possible to envisage stimulating effect beyond the therapeutic effect, for instance stimulating influence of muscle tissue, stimulating genital organs, and stimulating brain areas. Moreover, ultrasound treatment of tumors, for instance in the brain, has been practiced previously, and plaster units in accordance with the invention may also find a possible range of application here.

The invention claimed is:

1. A medical plaster system configured to deliver mechanical vibration energy to body tissue from the outside of the skin, the medical plaster system comprising:
   a flexible backing layer and an adhesive layer;
   at least one piezoelectric unit configured to emit tissue-influencing mechanical pulses or vibrations into tissue, located in or on said backing layer;
   an energizing unit for said at least one piezoelectric unit, said energizing unit comprising electronics configured to deliver electric pulses or oscillations in the range 80 Hz-3MHz, superposed on a slower oscillation to said at least one piezoelectric unit, said energizing circuit being attached to said backing layer or said adhesive layer; and
   a backing mass disposed between the flexible backing layer and the at least one piezoelectric unit, wherein the backing mass being more dense than the piezoelectric unit, the backing mass being at least ten times thicker than the at least one piezoelectric unit.

2. The medical plaster system of claim 1, wherein said energizing unit is situated on the medical plaster system, and is configured to control and/or energy supply from another, superior energizing circuit on another similar medical plaster system.

3. The medical plaster system of claim 1, wherein said energizing circuit is situated on the medical plaster system, and is configured to control and/or energy supply to other subordinate energizing circuits on other similar medical plaster systems.

4. The medical plaster system of claim 1, wherein said energizing circuit has its own battery.

5. The medical plaster system of claim 1, wherein said energizing circuit is situated on the medical plaster system, and is configured to receive control signals and/or power from an external operating unit, via wire or in a wireless manner.

6. The medical plaster system of claim 1, wherein said at least one piezoelectric unit is a piezoelectric foil.

7. A medical plaster system configured to emit tissue-influencing mechanical energy from the outside of a patient's skin, comprising:
   a number of plaster units each comprising a flexible backing layer and an adhesive layer, wherein every plaster unit has at least one piezoelectric unit configured to emit mechanical pulses or vibrations, located in or on said backing layer;
   a backing mass configured to radiate a larger part of the emitted energy from the piezoelectric unit into the patient's skin, the backing mass being disposed between the flexible backing layer and the at least one piezoelectric unit, wherein the backing mass being more dense than the piezoelectric unit, the backing mass being at least ten times thicker than the at least one piezoelectric unit,
   wherein the medical plaster system has at least one energizing circuit for the at least one piezoelectric unit, comprising electronics configured to deliver electric pulses or oscillations in the range 80 Hz-3 MHz, superposed on a slower oscillation, to said at least one piezoelectric unit; and wherein connecting means are provided between the plaster units configured to transmit control signals regarding interactive piezoelectric activity.

8. The medical plaster system of claim 7, wherein at least one of said plaster units of the system has its own energizing circuit attached to the backing layer or the adhesive layer.

9. The medical plaster system of claim 7, wherein said connecting means are wires between respective energizing circuits.

10. The medical plaster system of claim 9, wherein only one plaster unit has a battery, whereby the connecting wires are configured to transmit control signals and power.

11. The plaster system of claim 8, in which every medical plaster unit has its own energizing circuit and its own battery, wherein said connecting means are wireless connections configured to transfer control signals from one of said medical plaster units to remaining medical plaster units of the medical plaster system.

12. The medical plaster system of claim 11, wherein said main unit is connected regarding control and/or power, to an external operating unit, via wire or in a wireless manner.

13. The medical plaster system of claim 7, further comprising one single separate energizing circuit, connected by wire to the piezoelectric unit of every plaster unit.

14. The medical plaster system of claim 7, wherein the at least one piezoelectric unit is a piezoelectric foil.

15. The medical plaster system of claim 7, further comprising a positioning template for predetermined, grouped arrangement of the plaster units of the system in a given geometrical structure.

16. The medical plaster system of claim 1, wherein said energizing circuit is separate and linked to said medical plaster system via a wire connection.

17. The medical plaster system of claim 7, wherein said connecting means transfer power.

18. The medical plaster system of claim 9, wherein said connecting means connect the energizing circuit on one medical plaster unit and the piezoelectric unit on another medical plaster unit.

19. The medical plaster system of claim 15, wherein the geometrical structure of the positioning template is made relative to a particular tissue area.

* * * * *